United States Patent
Mead et al.

[19]

[11] Patent Number: 6,150,133
[45] Date of Patent: Nov. 21, 2000

[54] FERMENTATION CONTROL

[75] Inventors: David John Mead; Hendrik Van Urk, both of Radcliffe on Trent, United Kingdom

[73] Assignee: Delta Biotechnology Limited, Nottingham, United Kingdom

[21] Appl. No.: 09/142,778

[22] PCT Filed: Mar. 12, 1997

[86] PCT No.: PCT/GB97/00669

§ 371 Date: Sep. 11, 1998

§ 102(e) Date: Sep. 11, 1998

[87] PCT Pub. No.: WO97/33973

PCT Pub. Date: Sep. 18, 1997

[30] Foreign Application Priority Data

Mar. 13, 1996 [GB] United Kingdom .................. 9605255
Jan. 2, 1997 [GB] United Kingdom .................. 9700027

[51] Int. Cl.$^7$ .................................................. C12N 15/00
[52] U.S. Cl. .................. 435/69.1; 435/243; 435/244; 435/252.3; 435/252.33; 435/254.11; 435/254.21
[58] Field of Search .................. 435/69.1, 69.8, 435/69.6, 71.1, 243, 252.3, 252.33, 254.11, 254.21, 255.1, 255.2, 255.21, 244; 530/363, 364, 413, 414

[56] References Cited

U.S. PATENT DOCUMENTS 5,503,993  4/1996  Hayasuke et al. ............... 435/69.8
5,728,553  3/1998  Goodey et al. .................. 435/69.6

FOREIGN PATENT DOCUMENTS

| 0 283 726 | 9/1988 | European Pat. Off. . |
| 0 315 944 | 4/1994 | European Pat. Off. . |
| 200894/2 | 6/1983 | German Dem. Rep. . |
| 63/059838 | 3/1988 | Japan . |
| 2/109973 | 4/1990 | Japan . |
| 1 495 367 | 7/1989 | Russian Federation . |
| 2 177 801 | 1/1987 | United Kingdom . |

OTHER PUBLICATIONS

Belfares et al. Bioprocess Engineering. vol. 9, pp. 197–204, 1993.
Latrille et al. J. Fermentation and Bioengineering. vol. 74(1), pp. 32–38, 1992.
Turner et al (1994) *Biotech. Bioeng. 44*, 819–829.
Kell et al (1990) *Trends in Anal. Chem. 9*, 190–194.
Locher et al (1992) *J. Biotech. 25*, 55–73.
Locher et al (1992) *J. Biotech. 25*, 23–53.
Aristidou et al (1995) *Biotechnol. Prog. 11*, 475–478.

*Primary Examiner*—Remy Yucel
*Attorney, Agent, or Firm*—Naomi S. Biswas

[57] ABSTRACT

A process of culturing a microorganism in a culture medium in which process the addition of feed medium is controlled by using the production of a by-product as a measure of the culture conditions, characterized in that the by-product is an electrically charged metabolite produced by the microorganism, and in that the production of the metabolite is monitored by measuring the conductance of the culture medium. The metabolite may be acetate and the microorganism may be yeast which is genetically engineered to produce a desired polypeptide.

19 Claims, 8 Drawing Sheets

FERMENTATION CONTROL

FIELD OF THE INVENTION

The present invention relates to the control of fed-batch or continuous fermentation processes. In fermentation processes where a maximum biomass yield is required or the build-up of acids such as acetic acid might become toxic or may be detrimental to the product, the presence of such acids is undesirable.

BACKGROUND AND PRIOR ART

Correct control of medium addition rate to fermentation processes where accumulation of metabolites is to be prevented is a primary objective. Some microorganisms produce undesirable metabolites when fed at too high a medium addition rate. Examples are Bakers' yeast and *Escherichia coli* (De Deken, 1966; Doelle, 1981). Bakers' yeast will produce fermentation products such as ethanol and acetate when too much sugar is added (Fiechter et al, 1981). During the production of Bakers' yeast this will cause a loss of cell and product yield (Fiechter et al, 1981). The bacterium *E. coli* will produce acids such as acetic acid at sugar excess (Doelle, 1981). Also when microorganisms are used for the production of heterologous products the formation of these metabolites is undesirable, especially when these have a toxic or inhibitory effect. Acetate, ethanol and organic acids in general can be toxic to cell metabolism (Moon, 1983; Pampulha & Loureiro-Dias, 1989). This will become particularly apparent when growing mutant strains, which are often less robust than the wild-type strain. Therefore, good control of the feed addition rate to a fed-batch or continuous fermentation process is desirable.

Many ways of on-line computer control are possible. For example $CO_2$ evolution rates and $O_2$ consumption rates are often analysed on-line to calculate the so-called Respiratory Quotient (RQ) (Wang et al, 1977). The RQ is the $CO_2$ evolution rate divided by the $O_2$ consumption rate. Under sugar-limited conditions the RQ will be approximately 1·0 to 1·1, the exact value depending on the strain. However, when a culture of Bakers' yeast is fed at too high a sugar addition rate ethanol will be produced and the RQ values in that case will then be significantly higher than 1·1 (Wang et al, 1977; Fiechter et al, 1981). This then can be used to change the feed rate such that the RQ decreases (Wang et al, 1977).

EP 283 726 (Hitachi) and Turner et al (1994) disclose the control of fermentations by monitoring acetate levels, but the control was achieved by sampling the medium and using HPLC or similar discontinuous methods. HPLC has also been used to measure glucose levels in order to control acetate accumulation (Sakamoto et al, 1994).

The problem which is solved by the present invention is to provide an alternative and improved method of controlling such fermentations.

One aspect of the present invention provides a process of culturing a microorganism in a culture medium in which process the addition of feed medium is controlled by using the production of a by-product as a measure of the culture conditions, characterised in that the by-product is an electrically charged metabolite produced by the microorganism, and in that the production of the metabolite is monitored by measuring the conductance of the culture medium.

The evolution of electrically charged metabolites has not been used previously to control the addition of feed medium. RQ, for example, is 1 (one) when acetate is produced in a sugar fermentation, so RQ measurement is not useful, as this RQ value is near that obtained during sugar-limited growth. Electrical conductivity has been used to measure the formation of relatively large amounts of desired organic acids such as lactate in yogurt cultures and other lactobacillus fermentations (Latrille et al, 1992; Belfares et al, 1993), acetic acid production (SU-A-1 495 367) and for the control of salt content of fermentation cultures (Soyez et al, 1983). In the latter case, inorganic salts were added to the medium, and the technique simply measured those artificially added salts in order to maintain a desired salt concentration. Conductivity has also been used to measure cell density (JP-A-2 109 973). Conductivity has not been used to prevent and overcome the accumulation of undesirable acids such as acetate, of which even small amounts are indicative of the fermentation going awry. We have discovered that where the formation of organic acids such as acetate is undesirable, an increase in electrical conductivity can be measured on-line and used for a feed-back system to control the feed rate in a similar way as the RQ can be used. In this invention it is shown that increases in an on-line electrical conductivity signal during a fermentation process are sufficiently indicative of the formation of undesirable acids to be used to correct the feed addition rate in order to prevent and overcome accumulation of these acids. Hence, although for many years it has been known to measure (in an off-line biochemical assay) the production of acetate in order to see whether the fermentation control based on other parameters (eg $CO_2$ evolution) is working satisfactorily (see EP 315 944, 1989), nobody had measured acetate evolution electrically to control fermentation.

Obviously, the microorganism and the fermentation medium should be such that an electrically charged metabolite is potentially produced and the fermentation should be one in which controlling the addition of feed medium is desirable. Equally, the fermentation should not be one in which an electrically charged product is desired, for example a lactic acid fermentation. Microorganisms for which the present invention is useful include bacteria such as *E. coli* or Bacilli and fungi such as yeasts, for example Saccharomyces spp., especially *S. cerevisiae*, or filamentous fungi. However, the invention is in principle applicable also to the culturing of protozoa, plant cells and animal cells, for example insect cells or mammalian cells such as CHO (Chinese Hamster Ovary) cells.

The metabolite is typically an organic acid such as acetate, pyruvate, lactate or a citric acid cycle intermediate such as citrate, isocitrate, α-ketoglutarate, succinate, fumarate, malate or oxaloacetate.

The microorganism may be cultured to produce either biomass, a desired metabolite or a polypeptide which is native or heterologous to the microorganism. Hence, for example, the microorganism may be a yeast which contains and expresses a polynucleotide encoding human albumin. Advantageously, the polypeptide is secreted from the yeast into the surrounding medium and recovered therefrom.

The measurement of the conductivity is very sensitive and can detect acid concentrations as low as 1 mM. This means that it is a useful alternative, or addition, to the generally accepted use of on-line RQ measurements.

The control may be achieved by use of a probe, capable of measuring conductivity, inserted in a fermenter and linking the signal to an on-line computer. A conductivity probe can be very simply inserted in a standard pH probe port. A computer algorithm can then calculate the change in conductivity or conductance over a chosen time period. If the change in conductivity is greater than a chosen limit, a reduction in the feed medium addition rate will automatically be applied by the computer algorithm. This will then promote a co-consumption of the feed substrate and the accumulated metabolites present, and prevent further production thereof. The choice of time period and conductivity change limit will be dependant on the exact nature of the fermentation process.

DETAILED DESCRIPTION OF THE INVENTION

Preferred aspects of the invention will now be described by way of example and with reference to the accompanying drawings in which.

Figure 4:
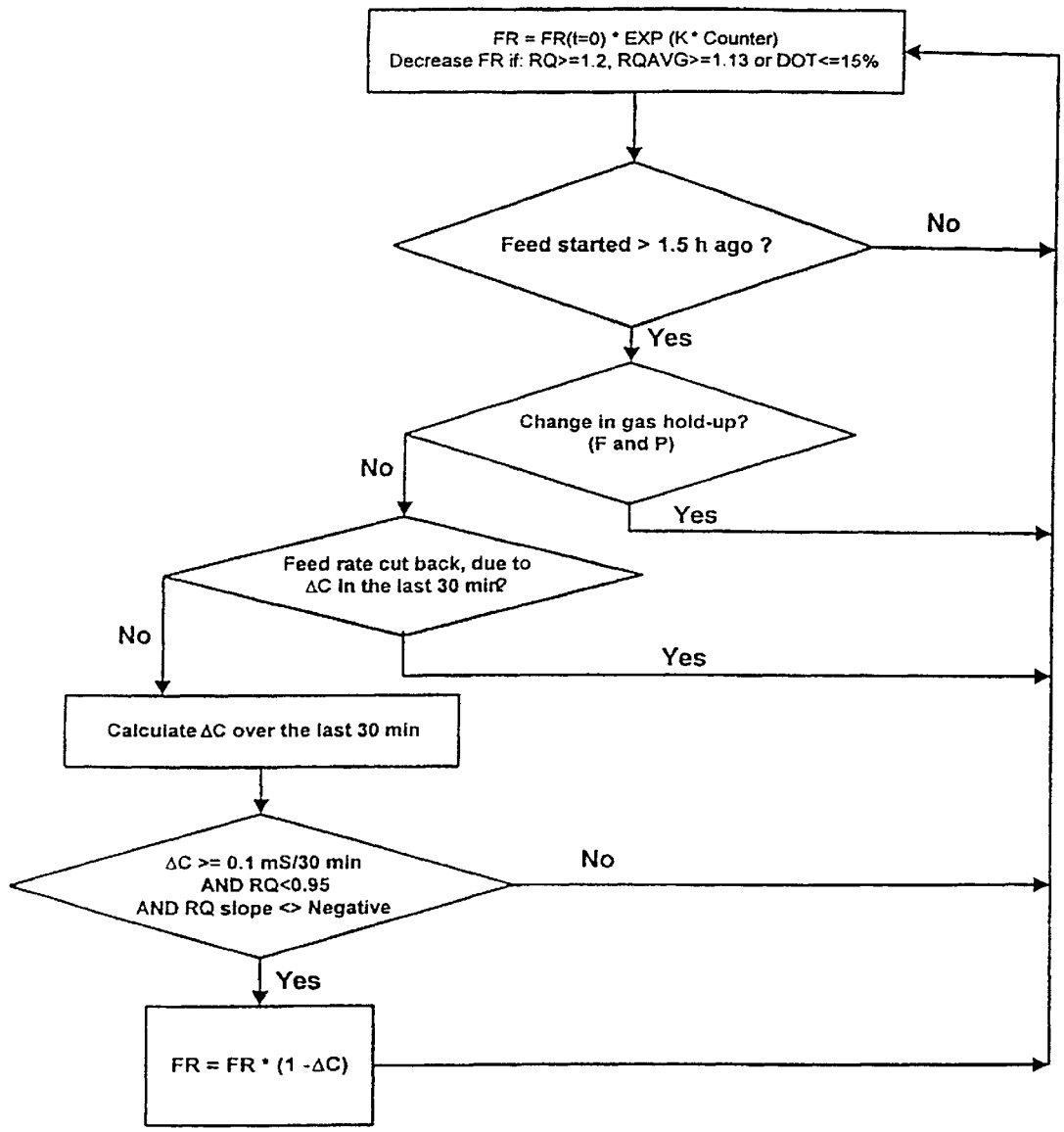
FIG. 4 is a simplified flow chart of a typical feed rate control algorithm, using the electrical conductance signal, that was used in the experiment represented in FIG. 5.
Figure 6:
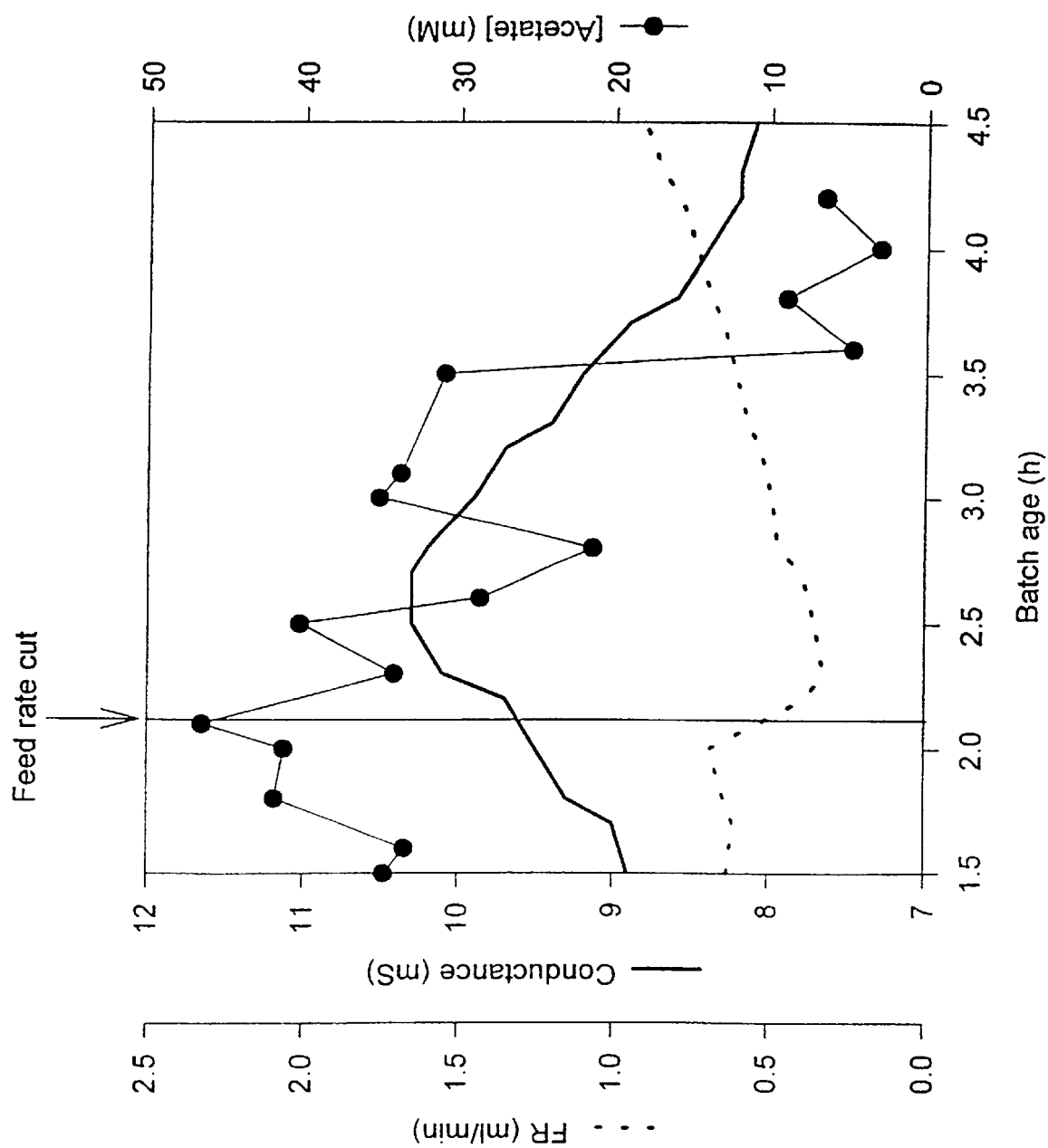

FIG. 6 shows some parameters of an experiment with the bacterial strain *E. coli* DH5α in which the conductance control algorithm shown in FIG. 4 was active. The factor K was set at 0.4 $h^{-1}$ in this experiment. Normally a factor 0.11 $h^{-1}$ would be used (Riesenberg et al., 1991).

Figure 7:
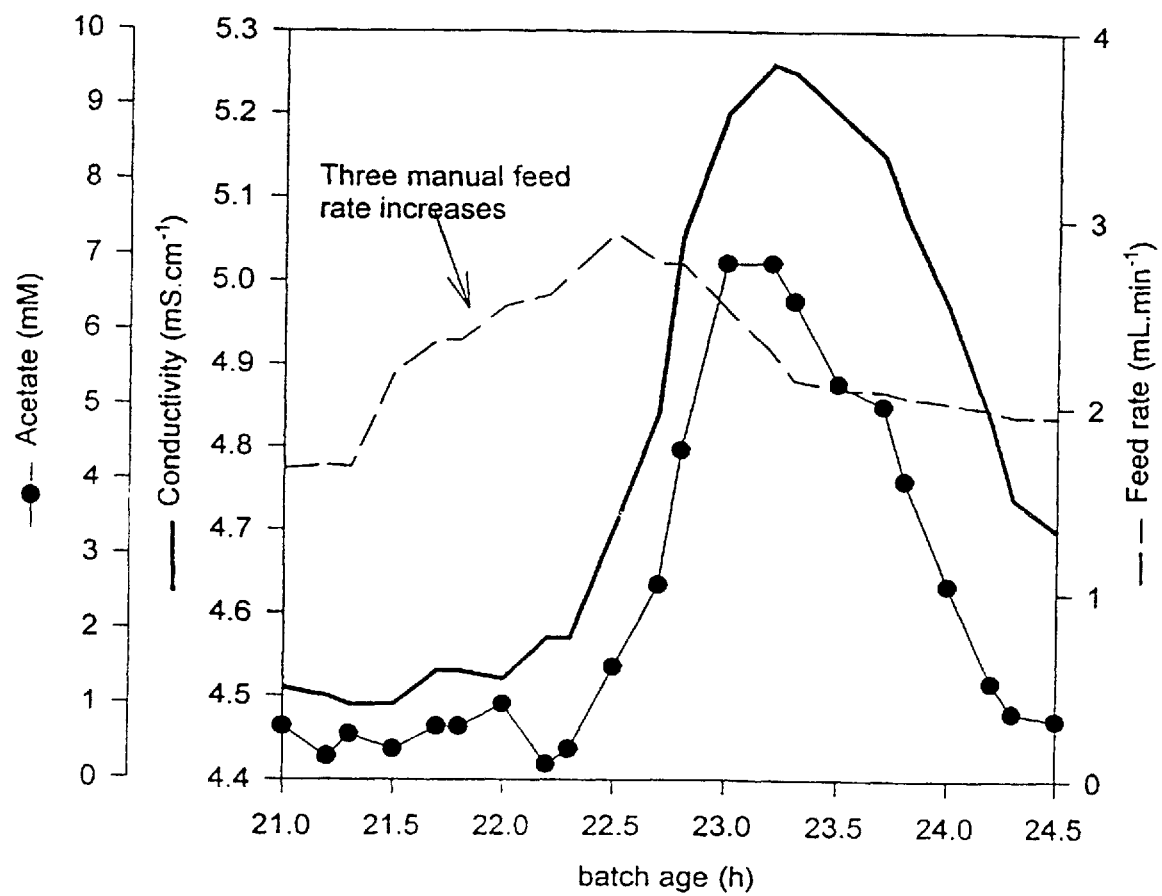

FIG. 7 shows some parameters of an experiment with the bacterial strain *E. coli* DH5α in which the feed rate was manually increased in three steps (21.3–22.3 h) and then was controlled by a similar algorithm as described in FIG. 4 but modified as described in Example 5.

Figure 8:
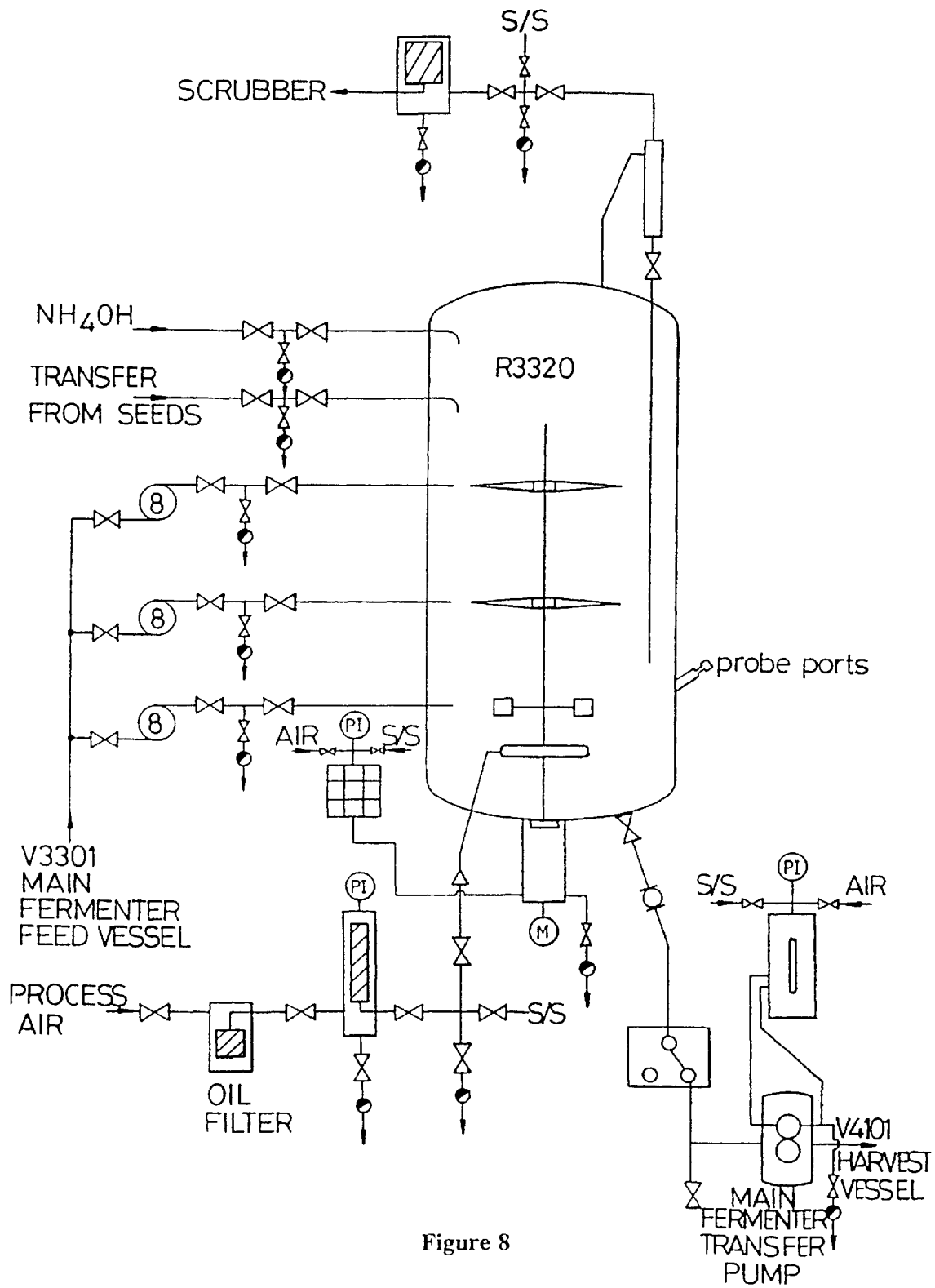

FIG. 8 is a schematic representation of a fermenter suitable for use in the process of the invention.

EXAMPLE 1

The Electrical Conductance During a Normal Fed-Batch Fermentation

Figure 1:
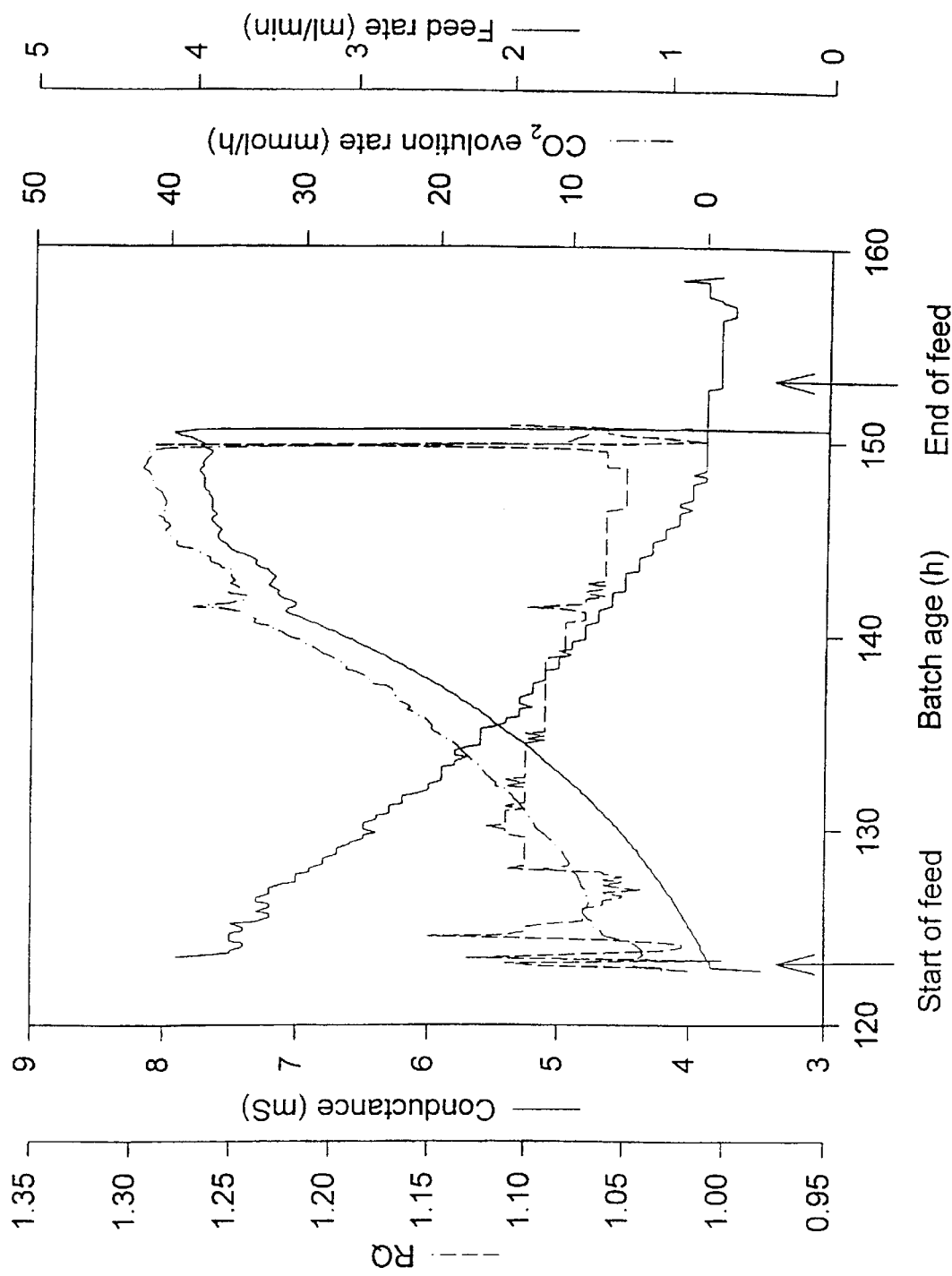
FIG. 1 is a representation of some key parameters during a fed-batch fermentation of a yeast strain producing recombinant human albumin. The points at which the feed addition was started and finished are indicated by arrows.

In order to determine the normal trend of the electrical conductance during a fed-batch fermentation (FIG. 1), we monitored the conductance on a fermentation control computer linked to an Aber Instruments (Aberystwyth, UK) Biomass Monitor 214A with an Aber Instruments Capacitance probe. The conductance signal was noisy due to the aeration of the fermenter. Therefore, the conductance had to be electrically filtered using the supplied filter number 2 on the Biomass Monitor 214A. As an alternative other conductivity probes and monitors can be used as long as the signal is adequately filtered to smooth the noisy signal. One such set up can be a Broadley James conductivity probe (from FT Applikon) linked to an MCD43 monitor (LTH Electronics) which uses a 3 min filter. All data in FIG. 1 are averaged over 10 min (due to the data storage limitations of the fermentation control computer).

The fermentation was performed as described by Clarke et al (1990), which is incorporated by reference. Essentially, the fermentation was as follows.

The fermentation was based on yeast transformed to express recombinant human albumin (rHA). The cloning strategy for construction of the yeast was as disclosed in EP 431 880.

A stock master cell culture in defined liquid medium (Buffered Minimal Medium (BMM) salts medium: Yeast Nitrogen Base [without amino acids and $(NH_4)_2SO_4$, Difco], 1.7 g/L; citric acid monohydrate 6.09 g/L; anhydrous $Na_2HPO_4$, 20.16 g/L; pH 6.5±0.2; $(NH_4)_2SO_4$, 5 g/L; sucrose is added to 20 g/L) was used to prepare running stocks (manufacturer's working cell bank) of process yeast suitable for the preparation of shake flask cultures by freezing aliquots of the culture in the presence of 20% (w/v) trehalose.

Shake Flask Culture. The yeast [cir°, pAYE316] was grown as an axenic culture physiologically suited for inoculation of the seed vessel. If timing of the seed vessel is to be reproducible, it is necessary to define the phase of growth (primary carbohydrate excess) and inoculum biomass (12±2 mg/L which requires a 100 ml inoculum per 10 liters of medium). One stock vial was inoculated into a shake flask containing 100 mL of BMM+2% (w/v) sucrose and the flask was incubated at 30° C. on an orbital shaker (200 rpm revolutions per minutes) until a cell dry weight (cdw) of 0.6–1.2 g/L (assessed by optical density at 600 nm) was obtained. This culture was then used to inoculate a seed fermentation vessel to a level of 12±2 mg/L.

Seed Fermentation. The inoculum for the main production fermenter was provided by growing the production organism, preferably *S. cerevisiae* [cir°, pAYE316], in a seed fermenter to a high cell dry weight of approx. 100 g/L. A fed-batch regime was followed so as to minimise the accumulation of ethanol and acetate and thus to maximise cell yield. The whole of each fermentation was monitored and controlled via a computer control system, such as the Multi-Fermenter Computer System (MFCS) software available from B. Braun (Germany). The software supplied by B. Braun is a Supervisory Control and Data Acquisition Package; similar packages are available from other companies. The algorithm is intended to control the addition of sucrose so that maximum biomass is achieved by avoiding the Crabtree effect, thereby minimising the production of ethanol and/or acetate. The fermentation vessel was subjected to a hot NaOH wash and pyrogen-free water (PFW) rinse. The heat sterilised vessel contained one volume of sterile MW10 nedium (Table 1) batch salts plus trace elements. An alternative medium is given in Table 2. Clearly, the initial conductivity will vary according to the constitution of the medium. The medium for rHA production can be ultrafiltered (10,000 Mol. Wt. cut-off) to remove endotoxins.

TABLE 1

| MW10 MEDIUM | | |
|---|---|---|
| Constituents | Batch Medium | Feed Medium |
| Salts | | |
| $KH_2PO_4$ | 2.74 g/L | 10.9 g/L |
| $MgSO_4.7H_2O$ | 0.58 g/L | 2.3 g/L |
| $CaCl_2.2H_2O$ | 0.06 g/L | 0.24 g/L |
| $H_3PO_4$ (85% w/w) | 0.88 ml/L | 1.76 ml/L |

TABLE 1-continued

MW10 MEDIUM

| Vitamins | | |
|---|---|---|
| Ca pantothenate | 20 mg/L | 180 mg/L |
| Nicotinic acid | 33.3 mg/L | 300 mg/L |
| m-Inositol | 20 mg/L | 180 mg/L |
| d-biotin | 0.133 mg/L | 0.8 mg/L |
| Thiamine.HCl | 16 mg/L | 32 mg/L |
| Trace element stock | 10 ml/L | 20 ml/L |
| Sucrose | 0* | 500 g/L |
| Trace Element Stock Constituents | | |
| $ZnSO_4.7H_2O$ | 3 g/L | |
| $FeSO_4.7H_2O$ | 10 g/L | |
| $MnSO_4.4H_2O$ | 3.2 g/L | |
| $CuSO_4.5H_2O$ | 0.079 g/L | |
| $H_3BO_3$ | 1.5 g/L | |
| KI | 0.2 g/L | |
| $Na_2MoO_4.2H_2O$ | 0.5 g/L | |
| $CoCl_2.6H_2O$ | 0.56 g/L | |

The trace elements were added to demineralised water, acidified with 35 ml/L of 98% $H_2SO_4$.
*20 g Sucrose/L was added to the batch medium at the 20 L seed fermenter stage. Any convenient method of sterilisation may be used, as may any depyrogenation method, for example ultrafiltration. The vitamins were always filter sterilised.

TABLE 2

MW11D MEDIUM

| Constituents | Batch Medium | Feed Medium |
|---|---|---|
| Salts | | |
| $KH_2PO_4$ | 4.66 g/L | 9.54 g/L |
| $MgSO_4.7H_2O$ | 0.98 g/L | 2.02 g/L |
| $CaCl_2.2H_2O$ | 0.10 g/L | 0.21 g/L |
| $H_3PO_4$ (85% w/w) | 1.63 g/L | 3.33 g/L |
| Vitamins | | |
| Ca pantothenate | 68 mg/L | 140 mg/L |
| Nicotinic acid | 114 mg/L | 233 mg/L |
| m-Inositol | 68 mg/L | 140 mg/L |
| d-biotin | 0.34 mg/L | 0.70 mg/L |
| Thiamine.HCl | 17.1 mg/L | 35 mg/L |
| Trace element stock | 10.2 mL/L | 21 mL/L |
| Sucrose | 0* | 500 g/L |
| Trace Element Stock Constituents | | |
| $ZnSO_4.7H_2O$ | 3 g/L | |
| $FeSO_4.7H_2O$ | 10 g/L | |
| $MnSO_4.4H_2O$ | 3.2 g/L | |
| $CuSO_4.5H_2O$ | 0.079 g/L | |
| $Na_2MoO_4.5H_2O$ | 0.5 g/L | |
| $CoCl_2.6H_2O$ | 0.56 g/L | |

The trace elements were added to demineralised water, acidified with 35 ml/L of 98% $H_2SO_4$.
*20 g Sucrose/L was added to the batch medium at the 20 L seed fermenter stage. Any convenient method of sterilisation may be used, as may any depyrogenation method, for example ultrafiltration. The vitamins were always filter sterilised.
After the medium was added to the vessel, the operating temperature of 30° C. was set, as well as the minimum stirrer speed, typically 400–500 rpm. The initial pH was adjusted with ammonia solution (specific gravity 0.901) using a pH controller set at 5.7 ± 0.2. 2M $H_2SO_4$ was also used as a pH corrective agent. Sucrose to 20 g/L, MW10 batch vitamins, and Breox FMT30 antifoam to 0.04 g/L are added to the vessel.

Sterile filtered air was introduced into the vessel at 0.5 vvm (ie 0.5 liter non-compressed air per liter of medium per minute), the medium was inoculated to 12±2 mg cell dry weight $L^{-1}$ from an axenic shake flask culture and the MFCS computer system was initiated. Following completion of the batch phase of growth (signalled by a dissolved oxygen tension increase of >15% in 30 min), addition of the feed medium was initiated, under control of the MFCS system. The control strategy was effectively the same as described below for the production fermenter. During the fermentation the airflow was increased in two steps in order to maintain a flow of approximately 1 vvm. Further Breox FMT30 was added to a final concentration of 0.3 g/L. The dissolved oxygen tension (DOT) was controlled at 20% air saturation by changing the stirrer speed. Once the stirrer speed could be increased further and the airflow rate reached its maximum value, the feed control algorithm (see below) controlled the feed rate such that the DOT did not decrease below 15% in order to prevent oxygen limited conditions that, otherwise, would lead to formation of fermentation products.

Also RQ was used as a feedback for the feed addition control. The feed rate was reduced every 10 min while $RQ \geq 1.2$. Moreover, a 120 min RQ average ($RQAVG_{120}$) was calculated to filter the noisy RQ signal (Goodey el al, 1996). The feed rate was reduced once every two hours by 20% if the value of $RQAVG_{120} \geq 1.13$. Due to an expected high RQ value at the start of a fermentation this $RQAVG_{120}$ control was not performed during the first 4 hours of the feed addition phase. At the end of the feed, the culture was transferred to a production vessel.

Production Fermentation. The production fermenter (FIG. 8) was inoculated with the culture grown in the seed fermenter (see above). The cell dry weight (CDW) concentration in the seed fermenter was normally greater than 80 g/L. The CDW concentration in the production fermenter just upon transfer of the seed fermenter culture was 0.25–1.00 g/L. Although it is preferred to initiate feeding within one hour, it can be delayed if necessary. The feed regime was intended to minimise the accumulation of ethanol and acetate, so as to maximise the cell and product yield.

The fermentation was carried out in a fermenter such as that shown in FIG. 8, designed to give optimum gas dissolution and bulk mixing. The fermenter was equipped with ports for, amongst other things, supplying feed medium, withdrawing medium at the end of the fermentation and introducing a probe for measuring electrical conductance. The vessel, which was subjected to a hot NaOH wash and PFW rinse, contained one volume of sterile MW10 (Table 1), batch salts and trace elements. This medium may be sterilized independently of the vessel either by heat or filter sterilisation. It has been found in accordance with the present invention that it is advantageous for the fermentation medium, such as MW10, to be free of ethylene diamine tetraacetic acid (EDTA), or a salt thereof, since its presence results in a significantly higher degree of coloured contaminants in the albumin produced.

The operating temperature was set at 30° C., and the stirrer speed regulated to be sufficient to maintain a homogeneous solution, typically about 50 rpm. The initial pH was adjusted with ammonia solution (SG 0.901) (controller set to 5.7±0.2). 2M $H_2SO_4$ nay be used as a second pH corrective agent. The MW10 batch vitamins were added, as was a suitable antifoam, as required (eg Breox FMT30 to 0.4 g/L). When the feed is started, the RQ over-ride control was disabled until OUR and CER values are sufficiently high to make control effective; the feed rate was reduced manually during this period if RQ was consistently >1.2.

The pH of the culture was kept constant at 5.5 by automatic addition of 17% (w/v) ammonia. The temperature was kept at 30° C. Sterile airflow was introduced at 0.5 vvm.

During the fermentation the airflow was increased in three steps in order to maintain a flow of approximately 1 vvm. This was measured by a continuous mass spectrometric analysis (Fisons VG Gas analyser). The fermentation was then run as above. Also the pressure in the fermenter was increased during the fermentation to approximately 0.5 bar g by using a Brooks pressure controller.

The feed rate was started at a feed rate, $FR_{start}$, that was necessary to achieve a growth rate of approximately 0.07 $h^{-1}$. Then the feed rate was increased, by computer control, according to the algorithm:

$$FR=FR_{start}EXP(K*Counter)$$

Where:

FR: feed rate (ml.min$^{-1}$)

K: the exponential constant which was kept at 0.07

Counter: a counter variable started at 0 and was increased by 0.0167 once every min. However, the counter variable was decreased:
a. by 0.0167 once every min if the dissolved oxygen tension (DOT) was less than 15%.
b. by 0.333 once very 10 min while $RQ \geq 1.2$.
c. by 0.223/K (resulting in a 20% feed rate reduction) once every two hours while $RQAVG_{120} \geq 1.13$ if the feed addition was started more than 4 h ago.

The result of such a fermentation is shown in FIG. 1. It can be concluded that the conductance trend in general sloped downwards during the course of the fed-batch fermentation.

EXAMPLE 2

The Electrical Conductance During a Phase where the Feed Rate was Suddenly Increased by 20%

Figure 2:
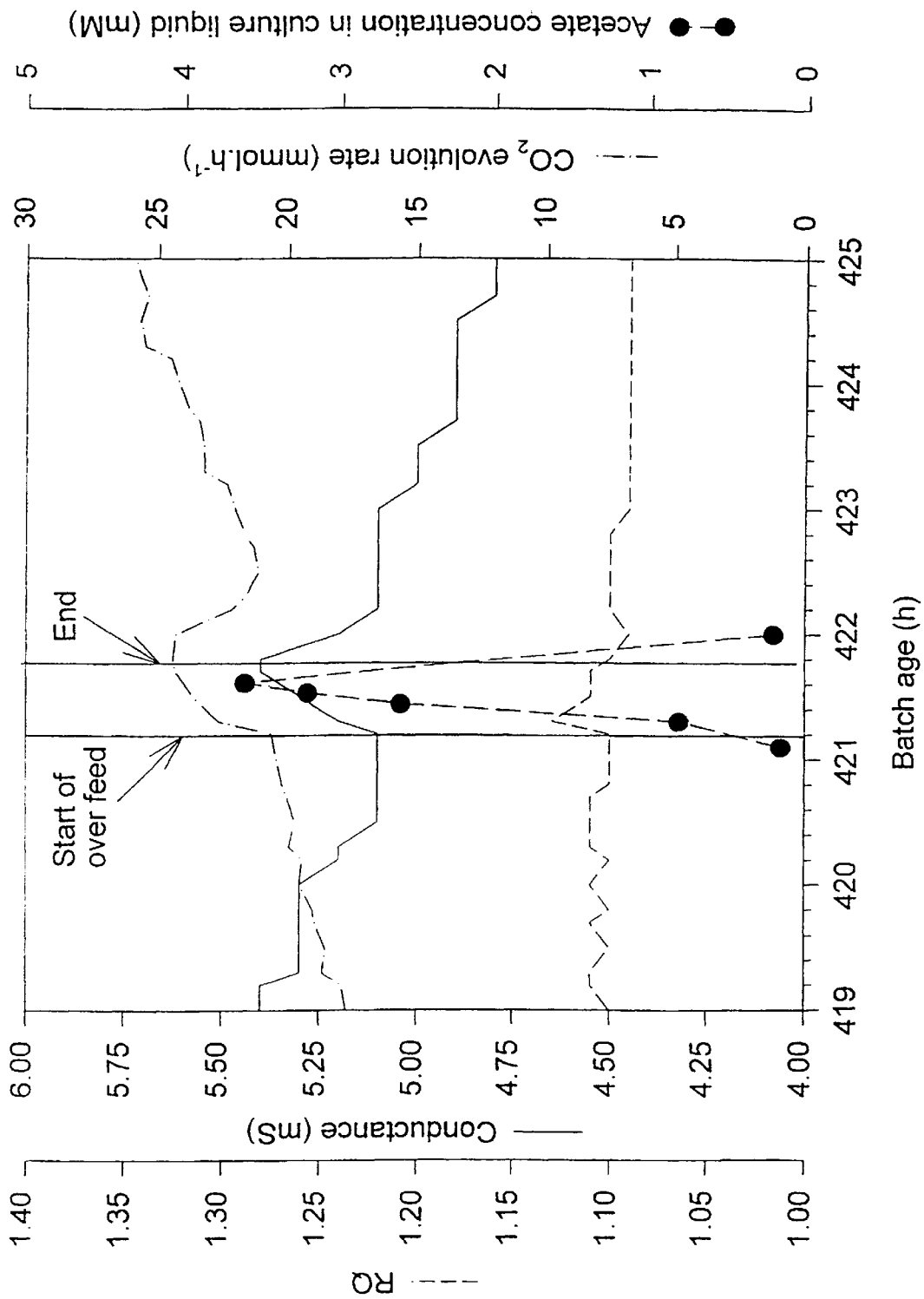
FIG. 2 shows parameters for part of a fed-batch fermentation during which, at the indicated time, a deliberate, sudden 20% feed rate increase was applied.

In order to establish the use of the conductance signal in the prevention and correction of acetate accumulation, a deliberate sudden step-increase of feed rate of 20% was applied at some stage in a carbon-limited fed-batch fermentation similar to the one described in Example 1. The results are shown in FIG. 2. It is shown that the conductance increased significantly during the period where the over-feed was applied. In fact, the RQ, a parameter often used in the control of Bakers' yeast production, did not show a significant increase. This shows the usefulness of the conductance signal because acetate production is undesirable during Bakers' yeast production. The increase in conductance correlated with an increase in acetate concentration in the culture as assayed in culture samples. The acetate was assayed using an enzymatic assay kit No. 148 261 from Boehringer Mannheim.

EXAMPLE 3

The Electrical Conductance During a Phase where the Feed Rate was Suddenly Increased by 40%

Figure 3:
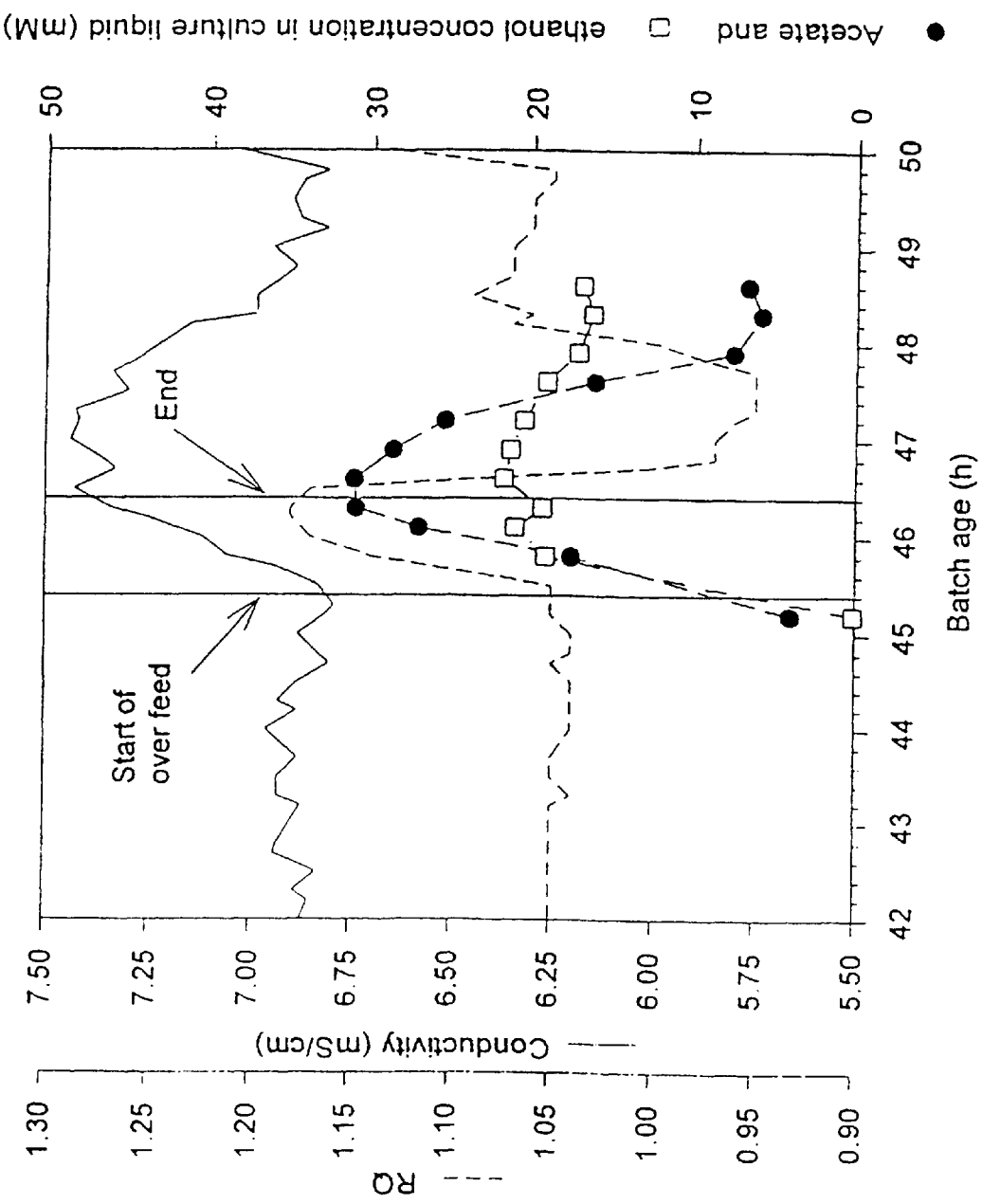
FIG. 3 is a similar experiment as shown in FIG. 2; however, in this case a 40% step increase was applied to the feed addition rate.

In a similar experiment as shown in Example 2 a sudden 40% feed rate increase was applied (see FIG. 3). The effects were more extreme than in Example 2, as would be expected. Also the RQ increased. However, a value of 1.2, which typically is used as a level to instigate feed rate reductions (see Example 2), was not reached. This again shows that conductance is a more sensitive physical control parameter than RQ.

EXAMPLE 4

The Use of a Feed Rate Control Algorithm Incorporating Electrical Conductance

In FIG. 4 a flow diagram is shown representing the feed addition control algorithm that was used in this Example.

The basis was the normal control algorithm as shown in Example 1. The condition where an airflow or pressure set point increase prevents the conductance feed control to be applied for 1 hour was necessary due to the fact that airflow and pressure increases will result in a small increase in conductance due to changes in gas holdup volume.

Moreover, in comparison with Example 1 the following additions were made to the feed rate control algorithm. The change in conductance (ΔC in mS) was measured over a time interval of 30 min. If the feed had been started within the last 1.5 h no feed back control would result. However, after that, in cases where the increase ΔC was $\geq 0.1$ mS over the chosen time interval, an automatic feed rate reduction would result. The actual size of the feed rate reduction was made dependent on the actual value of ΔC as follows: $FR_{reduced} = F_{original}*(1-\Delta C)$. No feed rate reduction would be applied if $RQ \leq 0.95$ or if the difference in $RQ_{30}$ ($RQ$ averaged over 30 min) over a time interval of 20 min: $RQ_{30} - RQ_{30\ 20\ min\ ago} \leftarrow -0.025$. Both these conditions indicate that the yeasts were already co-metabolising the feed substrate and fermentation products, thus abolishing the need for feed rate reductions.

Figure 5:
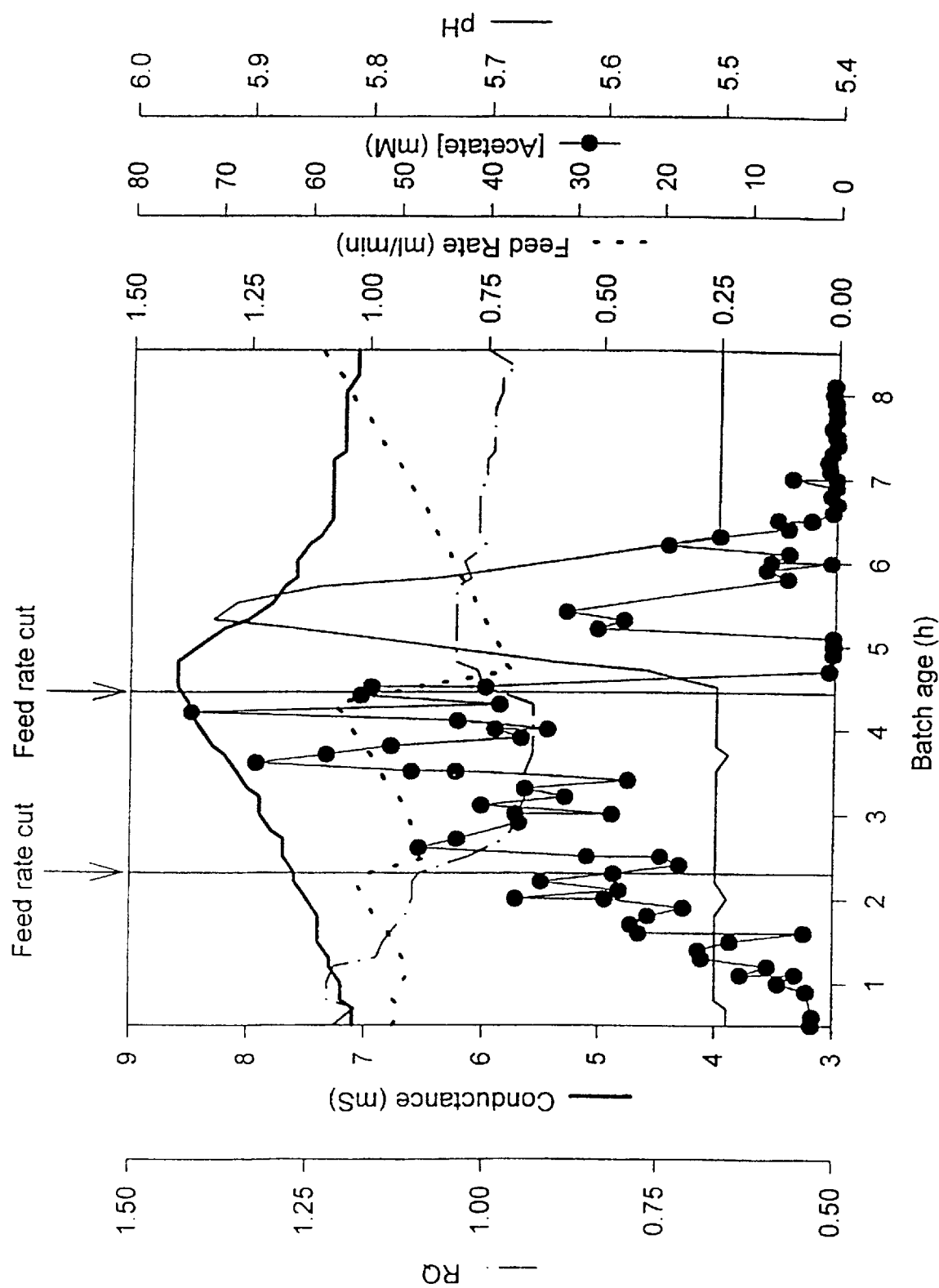
FIG. 5 is the representation of some parameters in an experiment during which the exponential factor K was set at 0.12 $h^{-1}$ which is higher than the usual value of 0.07 $h^{-1}$ for this yeast strain. During the experiment the algorithm using the conductance signal, of which the flow chart is shown in FIG. 4, was active.

An experiment was carried out where the exponential constant K (see Example 1) was set to 0.12 h$^{-1}$ which is so high that production fermentation products would be expected for this yeast strain which was the same as in Example 1. This was done to test the action of the control algorithm as shown in FIG. 4 and explained above. The results are presented in FIG. 5. The Figure shows a steady increase of conductance correlating with an increase in the acetate concentration. At 2.3 h (batch age) an automatic feed rate reduction was applied. This, however, was not sufficient and another automatic feed rate reduction was applied at 4.5 h (batch age). After that the acetate concentration reduced to 0 mM. Then the acetate concentration increased temporarily at batch age 5 h, whilst the conductance was decreasing. At the same time an excess of ammonium ions, which will have been added in the period up to 4.5 h (batch age) for pH control, was probably being consumed as judged by the pH changes in the culture. It is known that ammonium ions conduct electricity better than acetate ions (Owens, 1985) which explains the overall decrease of the conductance signal. Again a small peak in acetate concentration occurred at batch age 6 h. In this case the conductance increase was not enough to invoke a feed rate reduction. However, as judged by the reduction of the acetate concentration after that, further feed rate reductions were not necessary.

EXAMPLE 5

The Use of a Feed Rate Control Algorithm Incorporating Electrical Conductance with the Bacterial Strain *E. coli*

The bacterial strain *Escherichia coli* DH5α was grown in a fermenter using the medium described by Riesenberg et al (1991). The same control algorithm was used as in Example 4. However, the factor K was set at 0.4 h$^{-1}$. In FIG. 6 the result of the action of the control algorithm is illustrated. After a build up of acetate two automatic feed rate reductions resulted in a decrease of acetate from 45 to 5 mM.

This artificially high challenge to the fermentation showed that the system would work even under extreme conditions.

EXAMPLE 6

A Further *E. coli* Fermentation

This represents a more realistic (but still artificial) challenge to the equilibrium of a fermentation.

The bacterial strain *E. coli* DH5α was grown in a fermenter using the medium described by Riesenberg et al (1991). A similar control was used as in Example 4. However, the factor K was set at 0.1 h$^{-1}$. This would, under normal aerobic conditions, not lead to the production of organic anions. Then between the batch age 21.3–22.3 h (see FIG. 7) the feed rate was increased manually in three steps. Following this intervention, the conductivity increased and the feed rate was controlled according to the algorithm described in FIG. 4 with the following modifications. A control step was taken once every 10 min (as the conductivity increase was very steep) but the size of the feed rate reduction was a quarter of that described in FIG. 4. Thus the formula for feed rate was $FR_{reduced}=FR_{original}(1-\Delta C/4)$. As shown in FIG. 7 this controlled the fermentation such that the acetate produced was consumed by the cells. This example shows that the control algorithms may be optimised for different situations such as different organisms, growth rate and media types.

"Breox" is a trademark.

REFERENCES

Belfares et al (1993) *Bioprocess Eng.* 9, 197–204.

Clarke P. M., Collins S. H. and Mead D. J. (1990) "Fermentation of genetically engineered yeast in the presence of polyalkylene compound" WO 90/02808.

De Deken R. H. (1966) "The Crabtree effect: a regulatory system in yeast" *J. Gen. Microbiol.* 44, 149–156.

Doelle W. (1981) "New developments in the elucidation of the mechanisms of the Pasteur and Crabtree effects in bacteria" In: Moo-Young M., Robinson C. W. and Vezina C. (Eds.), *Advances in Biotechnology*, Pergamon Press, Vol. 1, pp 249–254.

Fiechter A., Fuhrmann G. F. and Kappeli O. (1981) "Regulation of glucose metabolism in growing yeast cells" *Adv. Microbiol. Physiol.* 22, 123–183.

Goodey A. R., Sleep D., van Urk, H., Berezenko S., Woodrow J. R. and Johnson, R. A. (1996). Process of high purity albumin production. International Patent Application. Publication No. WO 96/37515.

Latrille E., Picque D., Perret B. and Corrieu G. (1992) "Characterizing acidification kinetics by measuring pH and electrical conductivity in batch thermophilic lactic fermentations" *J. Ferment. Bioeng.* 74, 32–38.

Moon N. J. (1983) "Inhibition of the growth of acid tolerant yeasts by acetate, lactate and propionate and their synergistic mixtures" *J. Appl. Bacteriol.* 55, 453–460.

Owens J. D. (1985). Formulation of culture media for conductimetric assays: Theoretical considerations. *J. Gen. Microbiol.* 131: 3055–3076.

Pampulha M. E. and Loureiro-Dias M. C. (1989) "Combined effect of acetic acid, pH and ethanol on intracellular pH of fermenting yeast" *Appl. Microbiol. Biotechnol.* 31, 547–550.

Riesenberg D., Schulz V., Knorre W. A., Pohl H.-D., Korz D., Sanders E. A., Ross A. and Deckwer W.-D. (1991). High cell density cultivation of *Escherichia coli* at controlled specific growth rate. *J. Biotechnol.* 20: 17–28.

Sakamoto et al (1994) *J. Ferment. Bioeng.* 78, 304–309.

Soyez K., Schultz E. and Prause M. (1983) "Verfahren zur Steuerung der Kultivierung von Mikroorganismen" German Patent (DDR) 200894/2.

Turner C., Gregory M. E. and Thornhill N. F. (1994) "Closed-loop control of fed-batch cultures of recombinant *E. coli* using on-line HPLC" *Biotechnol. Bioeng.* 44, 819–829.

Wang H. Y., Cooney C. L. and Wang D. I. C. (1977) "Computer-aided Bakers' yeast fermentations" *Biotechnol. Bioeng.* 19, 69–86.

What is claimed is:

1. A process of culturing a microorganism in a culture medium in which process the addition of feed medium is controlled by using the production of a by-product as a measure of the culture conditions, wherein the by-product is an electrically charged metabolite produced by the microorganism, the formation of which metabolite is to be minimized, and wherein the production of the metabolite is monitored by measuring the conductance of the medium.

2. A process according to claim 1 wherein the microorganism is a fungus.

3. A process according to claim 1 wherein the microorganism is *E. coli*.

4. A process according to claim 1 wherein the metabolite is an organic acid.

5. A process according to claim 1 wherein the microorganism produces a polypeptide heterologous to the microorganism.

6. A process according to claim 5 wherein the polypeptide is human albumin.

7. A process of producing a fermentation product by culturing a microorganism which produces the material and then recovering the material, characterized in that the culturing is performed according to claim 1.

8. A process of culturing a microorganism in which process production of an electrically charged metabolite by the microorganism is to be minimized, the process comprising the steps of (i) providing a fermentation vessel adapted to contain a fermentation medium and the microorganism, the vessel having a first port to allow the supply of feed medium to be introduced into the vessel, control means to control the rate of the introduction of the feed medium, a probe to measure the electrical conductance of the fermentation medium, and a second port to allow removal of the fermentation medium from the vessel, (ii) introducing the microorganism and the fermentation medium into the vessel, (iii) measuring the electrical conductance of the fermentation medium with the probe at intervals during the course of the culturing process such that the probe generates a series of electrical signals indicative of the electrical conductance at the intervals, and (iv) supplying the electrical signals to the control means to control the supply of feed medium, wherein, in response to an undesirably high value of the conductance medium, the supply of feed medium is reduced.

9. A process according to claim 8 wherein the control means comprises a computer which operates an algorithm, the algorithm including a comparison between the measured electrical conductance signal and a predetermined value.

10. A process according to claim 8 wherein the control means comprises a computer which operates an algorithm, the algorithm including a calculation of a change in conductance over a given period, and a comparison of the change with a predetermined value.

11. A process according to claim 8 wherein the microorganism is a fungus.

12. A process according to claim 11 wherein the fungus is a yeast.

13. A process according to claim 12 wherein the yeast is a Saccharomyces.

14. A process according to claim 8 wherein the microorganism is *E. coli*.

15. A process according to claim 8 wherein the metabolite is an organic acid.

16. A process according to claim 15 wherein the organic acid is acetic acid.

17. A process according to claim 8 wherein the microorganism produces a polypeptide which is heterologous to the microorganism.

18. A process according to claim 17 wherein the polypeptide is human albumin.

19. A process of producing a fermentation product by culturing a microorganism which produces the fermentation product and then recovering the fermentation product, wherein the culturing is performed according to claim 8.

* * * * *